United States Patent
Xi et al.

(10) Patent No.: US 7,308,308 B1
(45) Date of Patent: Dec. 11, 2007

(54) METHOD TO MONITOR PROGRESSION OF ATRIAL FIBRILLATION AND TO DETECT ITS SUSCEPTIBILITY FOR TERMINATION

(75) Inventors: Cecilia Qin Xi, San Jose, CA (US); Sergio Shkurovich, Encino, CA (US)

(73) Assignee: Pacesetter, Inc., Sylmar, CA (US)

( * ) Notice: Subject to any disclaimer, the term of this patent is extended or adjusted under 35 U.S.C. 154(b) by 140 days.

(21) Appl. No.: 11/114,799

(22) Filed: Apr. 25, 2005

Related U.S. Application Data

(60) Provisional application No. 60/611,108, filed on Sep. 16, 2004.

(51) Int. Cl.
*A61N 1/39* (2006.01)
*A61N 1/365* (2006.01)
*A61N 1/37* (2006.01)

(52) U.S. Cl. .............. 607/14; 607/3; 607/4; 607/5
(58) Field of Classification Search .......... 607/3–6, 607/9, 14, 17, 28
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 5,476,483 A | 12/1995 | Bornzin et al. | 607/17 |
| 5,755,736 A * | 5/1998 | Gillberg et al. | 607/4 |
| 5,978,707 A * | 11/1999 | Krig et al. | 607/14 |
| 6,134,470 A * | 10/2000 | Hartlaub | 607/14 |
| 6,167,308 A * | 12/2000 | DeGroot | 607/14 |
| 6,731,981 B1 | 5/2004 | Hemmingsson et al. | 607/13 |
| 6,748,267 B2 * | 6/2004 | Shekhar et al. | 607/4 |
| 6,826,425 B2 * | 11/2004 | Bardy | 600/518 |
| 2002/0099414 A1 | 7/2002 | Evers et al. | 607/14 |
| 2005/0288725 A1 * | 12/2005 | Hettrick et al. | 607/17 |

FOREIGN PATENT DOCUMENTS

| | | |
|---|---|---|
| WO | WO 02/45792 A2 | 6/2002 |
| WO | WO 2005/006209 A1 | 1/2005 |

* cited by examiner

*Primary Examiner*—Kennedy J. Schaetzle
*Assistant Examiner*—Natasha Patel

(57) ABSTRACT

A method and apparatus for monitoring a patient's cardiac electrical activity is disclosed. The method includes determining a characteristic of the cardiac signals during a detected episode of atrial fibrillation. The method further includes comparing the characteristic to an atrial fibrillation therapy threshold and if the characteristic is less than or equal to the atrial fibrillation therapy threshold further comparing the characteristic to a self-termination threshold. If the characteristic is less than the self-termination threshold the method withholds anti-tachycardia therapy to allow the arrhythmia to self-terminate.

25 Claims, 5 Drawing Sheets

METHOD TO MONITOR PROGRESSION OF ATRIAL FIBRILLATION AND TO DETECT ITS SUSCEPTIBILITY FOR TERMINATION

CROSS-REFERENCE TO RELATED APPLICATIONS

This application claims the benefit of U.S. Provisional Application No. 60/611,108, filed Sep. 16, 2004.

FIELD OF THE INVENTION

The invention relates to implantable medical devices and more particularly to a method and apparatus for monitoring the progression of atrial fibrillation.

BACKGROUND OF THE INVENTION

Atrial fibrillation is a common and serious cardiac arrhythmia, affecting more than two million people in the United States alone. Clinically, atrial fibrillation involves an abnormality of electrical impulse formation and conduction that originates in the atria, that is, the upper chambers of the heart. Atrial fibrillation is characterized by multiple swirling wavelets of electrical current spreading across the atria in a disorganized manner. The irregularity of electrical conduction throughout the atria creates irregular impulse propagation through the atrioventricular node into the ventricle.

For example, impulse conduction can be extremely rapid, leading to reduced diastolic filling of the heart chambers and a corresponding reduction of the cardiac pumping action. Increased heart rate and loss of A-V synchrony may also exacerbate any underlying heart problems, such as heart failure, coronary blood flow, or other pulmonary disorders.

Alternatively, impulse conduction from the atria to the ventricles may be very limited so that atrial fibrillation can be sustained indefinitely, since the ventricles continue to drive circulation, albeit inefficiently. The risks of sustained atrial fibrillation are nevertheless serious including stroke and myocardial infarctions caused by the formation of blood clots within stagnant volumes in the atria.

Therefore, the relatively quick reversion to sinus rhythm of an episode of atrial fibrillation can reduce the risk of emboli formation or other complications. However, current devices do not sufficiently distinguish between sustained episodes of atrial fibrillation and atrial fibrillation episodes which are haemodynamically benign and likely to self terminate or those that are amenable to reversion with appropriately timed trains of pacing pulses.

SUMMARY

In one aspect of the present invention a method for monitoring a patient's cardiac electrical activity includes detecting an episode of atrial fibrillation and determining the atrial rate (frequency), or other characteristic of the cardiac signals during the episode of atrial fibrillation. Though the rate of atrial fibrillation is varying, it has a characteristic dominant rate or peak frequency. The present invention recognizes that atrial fibrillation segments with higher atrial rates (frequency) are more likely to persist, whereas those with a lower rate are more likely to terminate. Therefore one aspect of the present invention compares the atrial rate to an atrial fibrillation therapy threshold to identify episodes that are susceptible to self termination or termination through applied therapy. The present invention further compares the atrial rate to a self-termination threshold if the rate is less than or equal to the atrial fibrillation therapy threshold to identify episodes that are likely to self-terminate so that applied therapy is most likely not necessary.

In another aspect of the invention the method further includes updating an atrial fibrillation histogram to include information regarding the termination mechanism, episode length and atrial rate during the episodes that self terminate as well anti-tachycardia therapy that terminates an episode. This information by itself is clinically valuable since it provides an indicator of the progression of disease that augments current diagnostic trends. In addition, the stored information may also be used to optimize the atrial fibrillation therapy and self termination thresholds to better identify arrhythmias which are prone to termination due to anti-tachycardia pacing or self-termination.

BRIEF DESCRIPTION OF THE DRAWINGS

Further features and advantages may be more readily understood by reference to the following description taken in conjunction with the accompanying drawings, in which.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

In one embodiment of the present invention an implantable stimulation device monitors the patient to detect episodes of atrial fibrillation and automatically determines whether a detected episode of atrial fibrillation is susceptible to termination either naturally or in response to therapy. The present invention may be implemented in connection with any stimulation device that is configured or configurable to monitor intrinsic electrical cardiac activity. However, the advantages of the present invention may be best understood in connection with an exemplary stimulation device that is capable of being used in connection with the various embodiments that are described below.

It is to be appreciated and understood that other stimulation devices, including those that are not necessarily implantable, can be used and that the description below is given, in its specific context, to assist the reader in understanding, with more clarity, the inventive embodiments described herein. In the description that follows, like numerals or reference designators will be used to refer to like parts or elements throughout.

Figure 1:
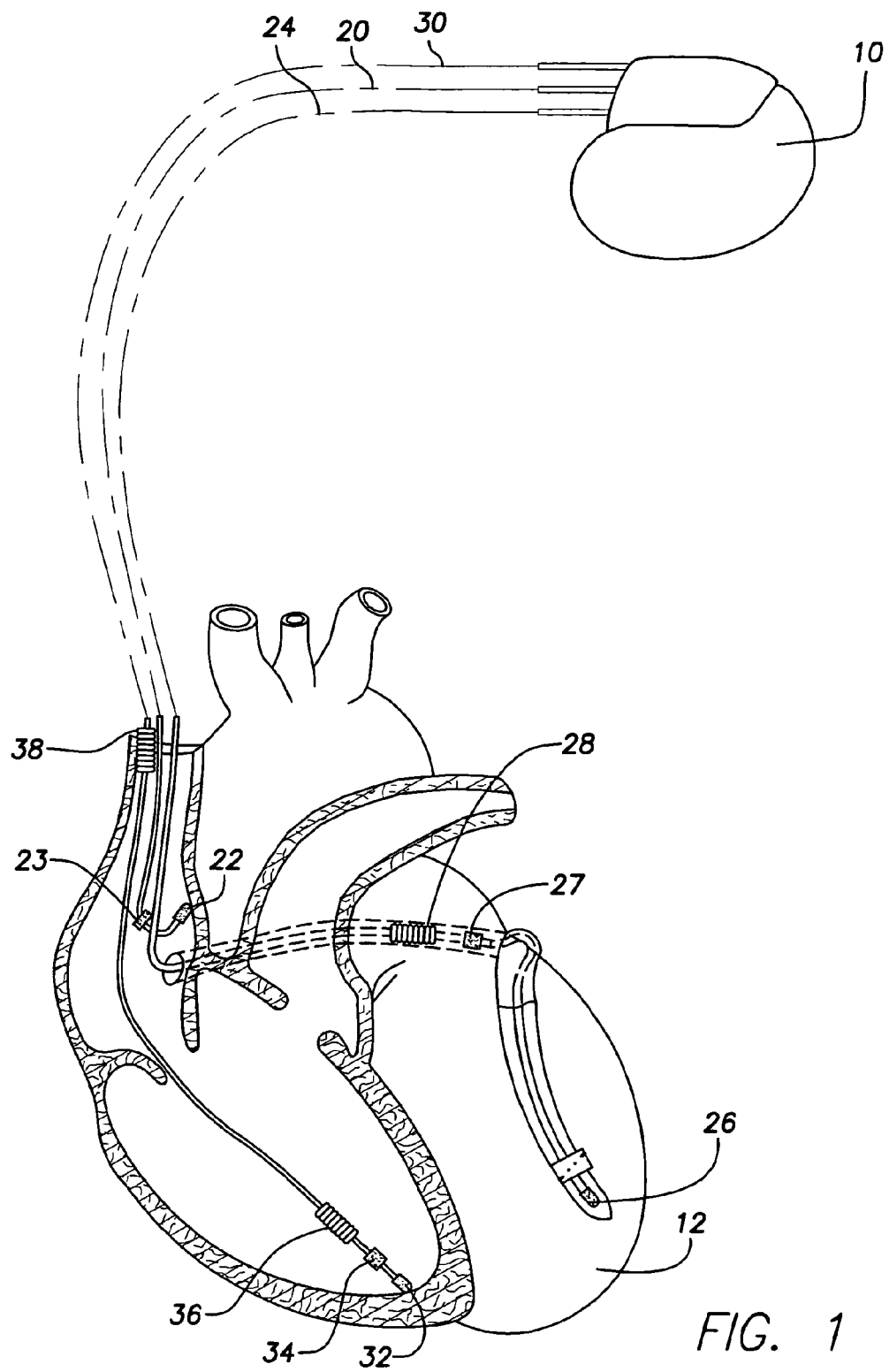
FIG. 1 is a simplified diagram of one embodiment of an implantable stimulation device in electrical communication with a patient's heart for delivering multi-chamber stimulation and shock therapy in accordance with one embodiment of the present invention.

FIG. 1 illustrates a prophylactic defibrillation and stimulation device 10 (also referred to herein as a prophylactic pacer/defibrillator) in electrical communication with a heart 12 by way of three leads 20, 24 and 30, suitable for delivering multi-chamber pacing stimulation therapy and ventricular defibrillation shock therapy. To sense atrial cardiac signals and to provide right atrial chamber stimulation therapy, device 10 is coupled to an implantable right atrial lead 20 having at least an atrial tip electrode 22 and an atrial ring electrode 23, which typically is implanted in the right atrial appendage.

To sense left atrial and ventricular cardiac signals and to provide left chamber pacing therapy, stimulation device 10 is coupled to a coronary sinus lead 24 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 10 is also shown in electrical communication with the patient's heart 12 by way of an implantable right ventricular lead 30 having, in this implementation, a right ventricular tip electrode 32, a right ventricular ring electrode 34, a right ventricular (RV) coil electrode 36 (or other electrode capable of delivering a shock), and superior vena cava (SVC) coil electrode 38 (or other electrode capable of delivering a shock). Typically, the right ventricular lead 30 is transvenously inserted into the heart 12 to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of sensing or receiving cardiac signals, and delivering stimulation in the form of pacing and shock therapy to the right ventricle.

Figure 2:
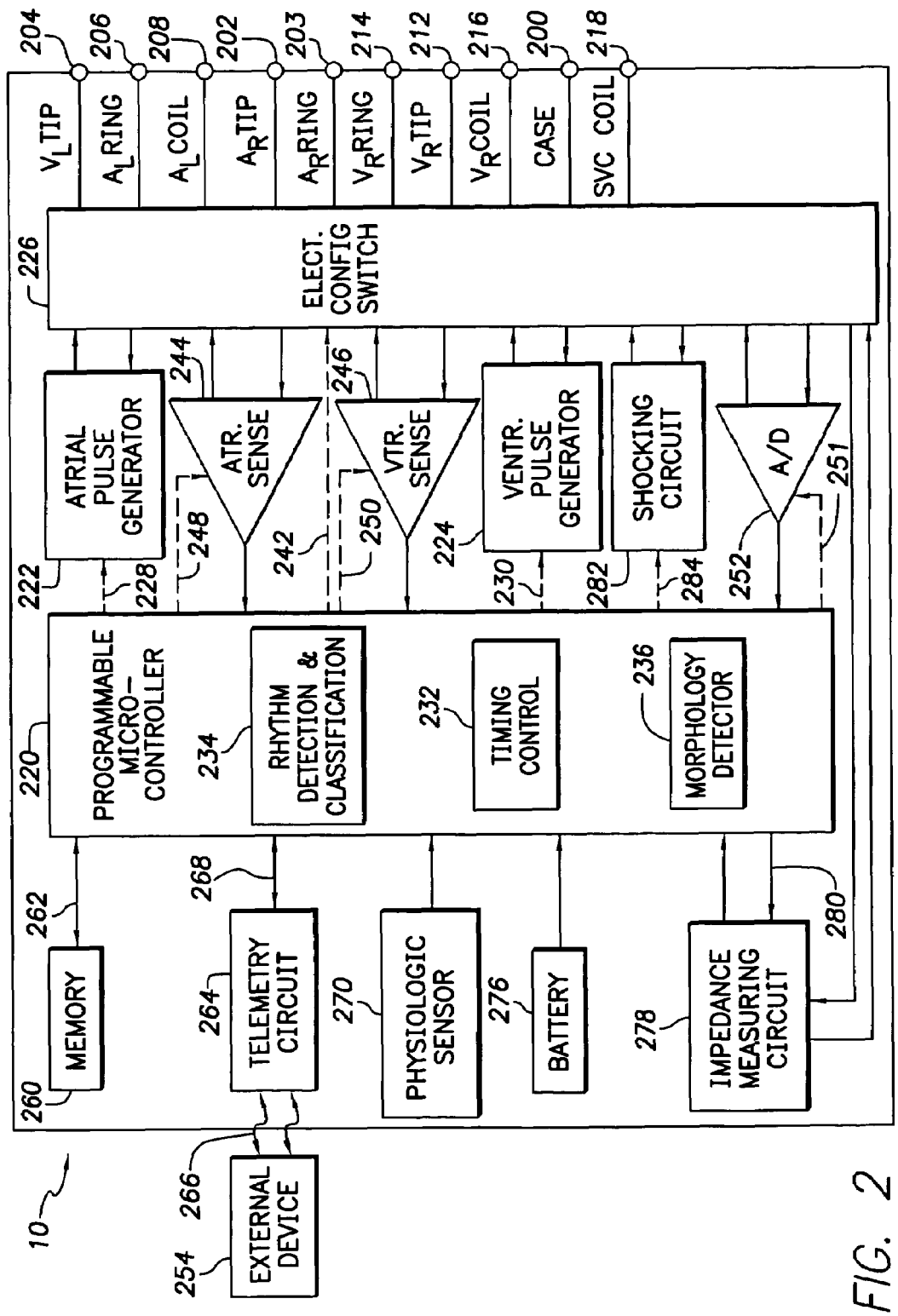
FIG. 2 is a simplified block diagram of a multi-chamber implantable stimulation device configured to provide cardioversion, defibrillation or pacing stimulation or any combination thereof in accordance with one embodiment of the present invention.

FIG. 2 shows an exemplary, simplified block diagram depicting various components of stimulation device 10. The stimulation device 10 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be selected to act as the return electrode for all "unipolar" modes. Housing 200 may further be used as a return electrode alone or in combination with one or more of the coil electrodes 28, 36 or 38 for shocking purposes. Housing 200 further includes a connector (not shown) having a plurality of terminals 202, 203, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 22. A right atrial ring terminal (AR RING) 203 may also be included adapted for connection to the atrial ring electrode 23. To achieve left chamber sensing, pacing, and shocking, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 26, the left atrial ring electrode 27, and the left atrial coil electrode 28, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry.

Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 20, the coronary sinus lead 24, and/or the right ventricular lead 30 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The microcontroller 220 is further coupled to a memory 260 by a suitable data/address bus 262, wherein the programmable operating parameters used by the microcontroller 220 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 10 may be non-invasively programmed into the memory 260 through a telemetry circuit 264 in telemetric communication via communication link 266 with an external device 254, such as a programmer, trans-telephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 10 (as contained in the microcontroller 220 or memory 260) to be sent to the external device 254 through an established communication link 266.

The stimulation device 10 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 10, it is to be understood that the physiologic sensor 270 may also be external to the stimulation device 10, yet still be implanted within or carried by the patient.

Examples of physiologic sensors that may be implemented in device 10 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 10, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 10 may employ lithium/silver vanadium oxide batteries.

The stimulation device 10 can further include magnet detection circuitry (not shown), coupled to the microcontroller 220, to detect when a magnet is placed over the stimulation device 10. A magnet may be used by a clinician to perform various test functions of the stimulation device 10 and/or to signal the microcontroller 220 that the external programmer 254 is in place to receive or transmit data to the microcontroller 220 through the telemetry circuits 264.

The stimulation device 10 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 20, the coronary sinus lead 24, and the right ventricular lead 30 through the switch 226 to sample cardiac signals across any pair of desired electrodes.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 10 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 20, coronary sinus lead 24, and the right ventricular lead 30, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations.

The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 10 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia.

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

In the case where the stimulation device 10 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220.

Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 200 may act as an active electrode in combination with the RV coil electrode 36, and/or as part of a split electrical vector using the SVC coil electrode 38 or the left atrial coil electrode 28 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Atrial fibrillation is a progressive disease. In the early stages atrial fibrillation is often paroxysmal in nature, lasting only a few seconds and self terminating with little patient discomfort. However, there is considerable evidence that spontaneous terminating (paroxysmal) atrial fibrillation is a precursor to the development of sustained atrial fibrillation which is associated with stroke and myocardial infarction, as well as mortality, fatigue, and heart failure. One embodiment of the present invention therefore identifies atrial fibrillation episodes which are likely to spontaneously terminate and which episodes are susceptible to termination through application of one or more pacing regimes to enable early termination of atrial fibrillation episode to slow the progression of the disease.

In one embodiment of the invention, a classifier classifies intracardiac electrograms taken during episodes of atrial fibrillation into various classes, i.e. self-terminating, sustaining or the like. In one embodiment, the classifier utilizes one or more fibrillation classification thresholds developed and optimized through operation on a database of measured intracardiac electrograms which were measured during episodes of atrial fibrillation.

In this embodiment the electrograms stored in the database are classified by experts as non-terminating episodes of atrial fibrillation which did not terminate for the duration of the long-term recording, and episodes of atrial fibrillation that terminated almost immediately after the end of the stored electrogram and those that terminated shortly after the end of the stored electrogram. In one embodiment the classification thresholds are developed by comparing the result of a classification decision using various values of the classification thresholds on the stored electrograms to the expert classifications and seeking parameters for the classification thresholds which maximize agreement between the classifier's decisions and the expert's classification.

Figure 3:
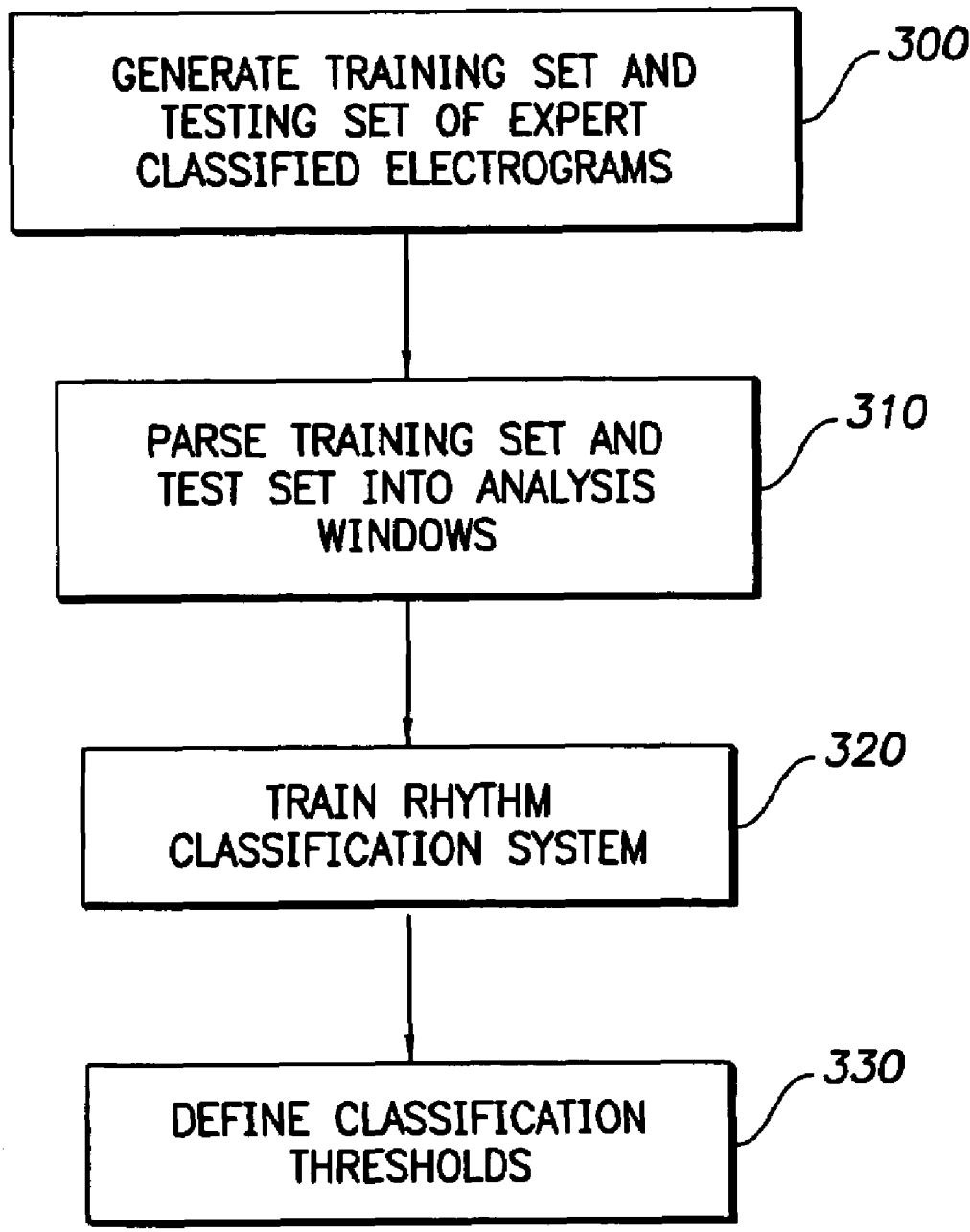
FIG. 3 is a flow chart illustrating one method for generating threshold for use in detecting episode of atrial fibrillation in accordance with one embodiment of the present invention.

The flow chart of FIG. 3 illustrates one method for generating fibrillation classification thresholds that can be stored in an implantable stimulation device for use in detecting and classifying atrial fibrillation episodes. In one embodiment of the present invention a collection of measured intracardiac electrograms is randomly divided into a training set of intracardiac electrograms and a testing set of electrograms 300. In this embodiment, the training set electrogams are used to define classification thresholds which can be used to classify episodes of atrial fibrillation as a sustaining episode or an episode that will self-terminate. The performance of the classifier using the classification thresholds is then verified on the testing set of electrograms.

In general, the training set and testing set may comprise any type of electrophysiological information (e.g. ECG, EGM) obtained from the subject of interest or from a general collection of heart data such as from the "Spontaneous Termination of Atrial Fibrillation: A challenge from PhysioNet and Computers in Cardiology 2004" database. This database is composed of eighty surface ECG recordings of atrial fibrillation episodes which are classified into the three different groups.

In one embodiment of the present invention each electrogram segment is parsed in an analysis window and sampled at a predetermined sampling rate 310. One of skill in the art will appreciate that the window length and sampling rate used to generate the windows of electrogram data from which the classification thresholds are determined can affect the performance of the classification system. For example, varying the window length creates tradeoffs between the response time of the classifier and the sensitivity and specificity of the classification system as well the computational duty cycle of the classifier.

In one embodiment one or more electrogram features that are indicative of the duration of the atrial fibrillation episode are used as classification thresholds. For example, electrophysiologic remodeling of atrial fibrillation suggests that atrial fibrillation tends to be self supporting and at a higher rate when sustained. Thus, atrial fibrillation episodes with higher peak frequencies or atrial rates in an analysis window are more likely to be sustained while episodes with lower frequencies or atrial rates are more likely to self-terminate.

Therefore, in one embodiment terminating episodes of atrial fibrillation are differentiated from sustained episodes in accordance with the peak frequency or atrial rate during the analysis window. In this embodiment the classification thresholds are developed or trained by comparing the results of episode classifications, using various peak frequency or atrial rate thresholds to the expert classifications 320 and seeking values for the classification thresholds which maximize agreement between the classifier's decisions and the expert classifications 330. The optimized classification thresholds are then stored in an implantable stimulation device for use in detecting and classifying cardiac arrhythmias.

Figure 4:
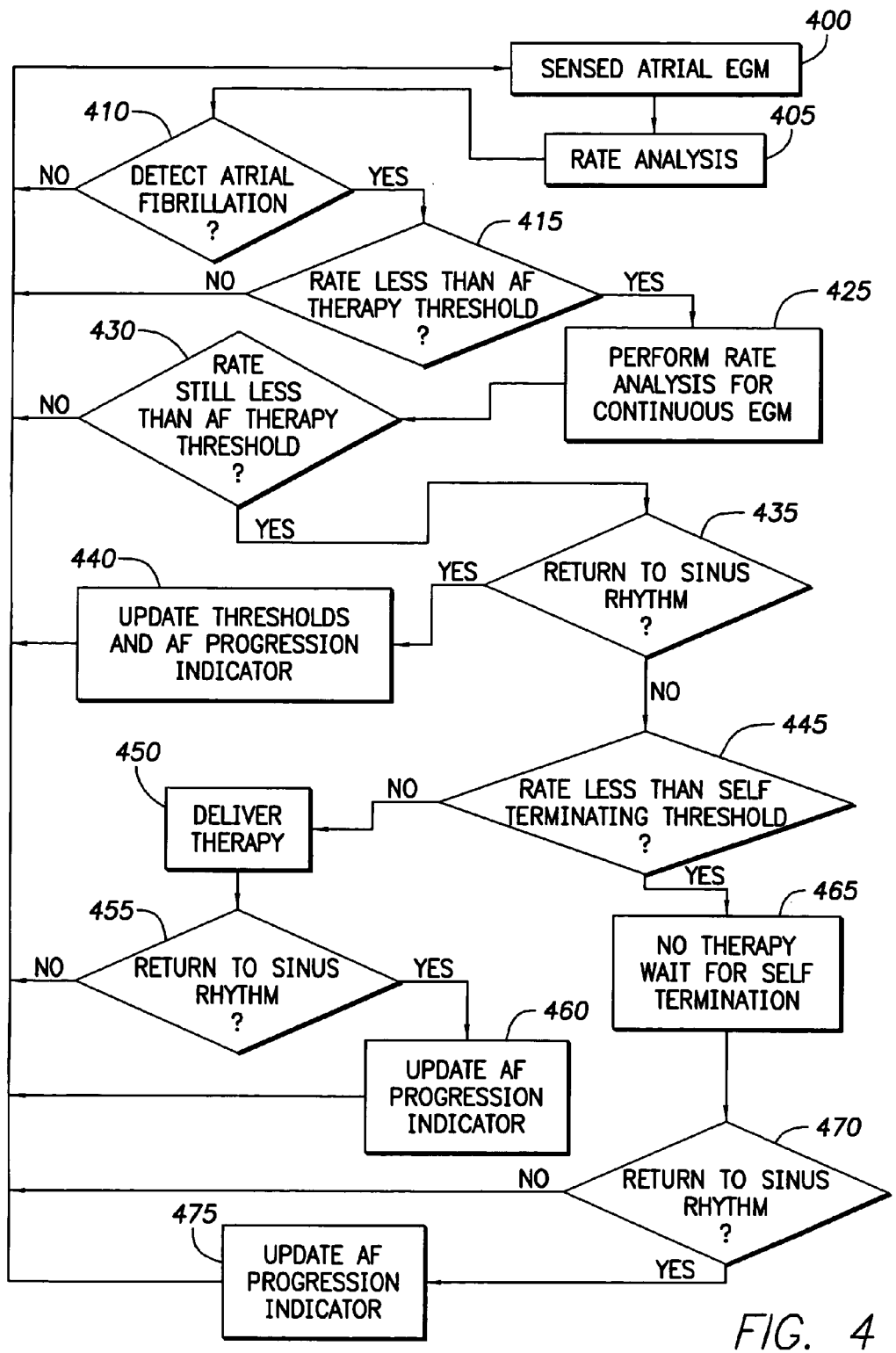
FIG. 4 is a flowchart showing a method for detecting atrial fibrillation events that are susceptible for termination based on the atrial rate of the atrial EGM in accordance with one embodiment of the present invention.

For example FIG. 4 is a flowchart illustrating the operation of one embodiment of a stimulation device to detect, classify and if appropriate respond to atrial fibrillation episodes. In this flow chart, the various operational steps are summarized in individual "blocks". Such blocks describe specific actions or decisions that are carried out during operation of the illustrated device 10. Where a microcontroller (or equivalent) is employed, the flow chart presented herein provides the basis for a "control program" that may be used by such a microcontroller (or equivalent) to effectuate the desired control of the stimulation device.

In this embodiment of the present invention an implantable stimulation device acquires 400 and samples an intracardiac atrial electrogram to determine the current atrial rate 405 and to detect the onset of atrial fibrillation 410. The length of the intracardiac atrial electrogram may be varied in accordance with device memory or other device specific features. In one embodiment a segment length of 10-20 seconds is acquired and sampled to monitor the progression of and susceptibility to termination of an episode of atrial fibrillation. A far field cardiac electrogram could also be used for analysis if atrial activity is separated from other activity (e.g. ventricular).

In this embodiment the micro-controller of the implantable device determines the intrinsic atrial fibrillatory rate using frequency analysis, zero crossing count, intrinsic event detection (i.e. using morphology, threshold detection, or the like), or other reliable mechanisms which are compatible with implantable applications. In one embodiment, the micro-controller of the implantable device compares the rate to an atrial fibrillation therapy threshold rate 415, which discriminates between arrhythmias which are susceptible to termination and those which are not. In this embodiment, if the current atrial rate is greater than the atrial fibrillation therapy rate threshold the fibrillation episode is not likely to terminate, either naturally or through the application of stimulation therapy. In this instance the device reverts to monitoring signals on the atrial channel 400.

Otherwise, the micro-controller of the implantable device continuously analyzes the current atrial rate for a predetermined period of time 425 to determine if the current rate remains less than the atrial fibrillation therapy threshold 430. In this embodiment if the atrial rate during the predetermined period exceeds the atrial fibrillation therapy rate threshold the implantable device reverts to monitoring signals on the atrial channel 400.

If the atrial rate is less than the atrial fibrillation therapy threshold throughout the pre-determined period, the micro-controller determines whether the patient has returned to sinus rhythm 435. If the patient has returned to sinus rhythm the micro-controller updates the therapy threshold and a self termination threshold to reflect the rate at which the arrhythmia terminated. The device also updates an atrial fibrillation progression indicator histogram 440 to include statistics such as the length of the fibrillation episode, the maximum rate (and statistical variations thereof) as well as the atrial rate when the episode self-terminated. The device then returns to monitoring signals on the atrial channel 400.

However, if the patient does not return to sinus rhythm the micro-controller compares the current rate to the self terminating threshold 445. In one embodiment the self terminating threshold is less than the fibrillation therapy threshold and is used to identify episodes of atrial fibrillation that are likely to self-terminate without therapeutic intervention. If the current atrial rate is not less than the self terminating threshold rate the implantable device delivers anti-tachycardia therapy to terminate the arrhythmia 450.

One technique for preventing or terminating dysrhythmias, such as atrial fibrillation is to overdrive pace the heart wherein the implantable cardiac stimulation device applies electrical pacing pulses to the heart at a rate somewhat faster than the intrinsic atrial rate of the patient. In other words, a slight artificial tachycardia is induced and maintained in an effort to terminate the fibrillation episode and to prevent the progression of the disease. Alternatively, the device may deliver a cardioversion shock to the atria to terminate the fibrillation episode.

In some embodiments, the device applies cardioversion therapy only if overdrive pacing fails to terminate the arrhythmia or in place in of overdrive pacing altogether. In addition, the device may deliver a defibrillation shock pulse if cardioversion fails to terminate the fibrillation episode.

The micro-controller then determines if the patient has returned to sinus rhythm 455. If so the micro-controller updates the atrial fibrillation progression indicator histogram 460 to include statistics such as the length of the fibrillation episode, the maximum rate during the episode (and statistical variations thereof as well as the stimulation therapy that successfully terminated the episode. Additional arrhythmia diagnostics including histograms of paced and sensed events, electrograms, activity variance and trends of lead impedance may also be stored. Such information is useful not only in optimizing device programming but also in the management of the patient's arrhythmias and other conditions.

In this embodiment, if the current atrial rate is below the self-terminating threshold the micro-controller withholds therapy and waits a predetermined period for the fibrillation episode to self-terminate 465 and for the patient to return to sinus rhythm 470. If the patient returns to sinus rhythm the micro-controller again updates the atrial fibrillation progression indicator histogram 475 to include statistics such as the length of the fibrillation episode, the maximum rate (and statistical variations thereof as well as the atrial rate when the episode self-terminated. If the patient does not return to sinus rhythm the micro-controller returns to monitoring signals on the atrial channel 400.

One of skill in the art will appreciate that the performance of the present invention may be optimized for individual patients in accordance with the statistical data collected in the atrial fibrillation progression indicator histogram. For example, in some embodiments the threshold levels may be optimized to account for the patient specific nature of atrial fibrillation. For instance, in one embodiment the implantable device initially operates with a universal atrial fibrillation therapy threshold and self terminating threshold developed on a known database of electrograms as programmed by the physician. In operation the device then monitors the atrial fibrillation progression indicator histogram and updates the operational thresholds in response to actual patient specific fibrillation data stored in the histogram.

In one embodiment, if the ongoing atrial fibrillation episode does not self terminate after a predetermined period the micro-controller lowers the self termination threshold. The device will therefore apply anti-tachycardia therapy at a lower atrial rate in response to the detection of ongoing atrial fibrillation episodes. In this embodiment, the micro-controller returns to monitoring the signals sensed on the atrial channel 400 if the fibrillation episode does not self terminate. If necessary the device then uses the adjusted self-termination threshold 435 to decide whether to deliver or withhold anti-tachycardia therapy in response to the ongoing detection of the atrial fibrillation 430. In addition a physician may update the fibrillation thresholds in response to changes in the patient's medications or other factors that may alter the characteristics or progression of the disease.

Further, in one embodiment of the present invention the micro-controller periodically examines the progression of the disease as documented in the atrial fibrillation progression indicator histogram and adjusts the thresholds accordingly. In this embodiment the device may also set a flag for transmission to the physician, either during a follow-up visit or through an RF Transmission or other wireless communication means to a local communications device, noting the progression or regression of the disease.

In addition, drugs are often effective at restoring normal heart rhythms. Therefore, in one embodiment of the present invention the implantable medical device of FIG. 2 is coupled to an implantable drug pump which administers one or more anti-arrhythmia drugs to alleviate one or more abnormal heart rhythms. In this embodiment a drug pump, with multi-drug dispensing capability, is coupled to a catheter to discharge an anti-arrhythmia drug directly into the atrium or more generally into the blood stream. Drugs that can defibrillate the atria are amiodarone, bethanidine, clofilium, encainide, esmolol, flecainide, ibutilide, phenotiazine derivatives, procainamide, propafenone, quinidine, or the like.

In one embodiment the micro-controller of the implantable stimulation device monitors the results of the anti-tachycardia pacing and or the length of an ongoing atrial fibrillation episode. In the event that the anti-tachycardia pacing terminates the fibrillation episode, the device resumes monitoring the atrial rate. In the alternate, if the anti-tachycardia pacing is unsuccessful in terminating the fibrillation episode and or the fibrillation episode continuous for a predetermined period of time, the micro-controller instructs the drug pump to inject a predetermined drug dosage into the atrium of the patient. In other embodiments, the implantable stimulation device advises the patient to take a prescribed anti-arrhythmia drug by emitting an audible alarm or transmitting an RF signal or other wireless communication means to an external communications device or the like.

In one embodiment of the present invention, the implantable stimulation device tracks the drug injection history and the anti-tachycardia pacing effect as well as the self termination of detected fibrillation episodes. In this embodiment, the micro-controller can then control the administration of anti-arrhythmia drugs in accordance with a predetermined schedule or maximum dosage regime as established by the treating physician.

Figure 5:
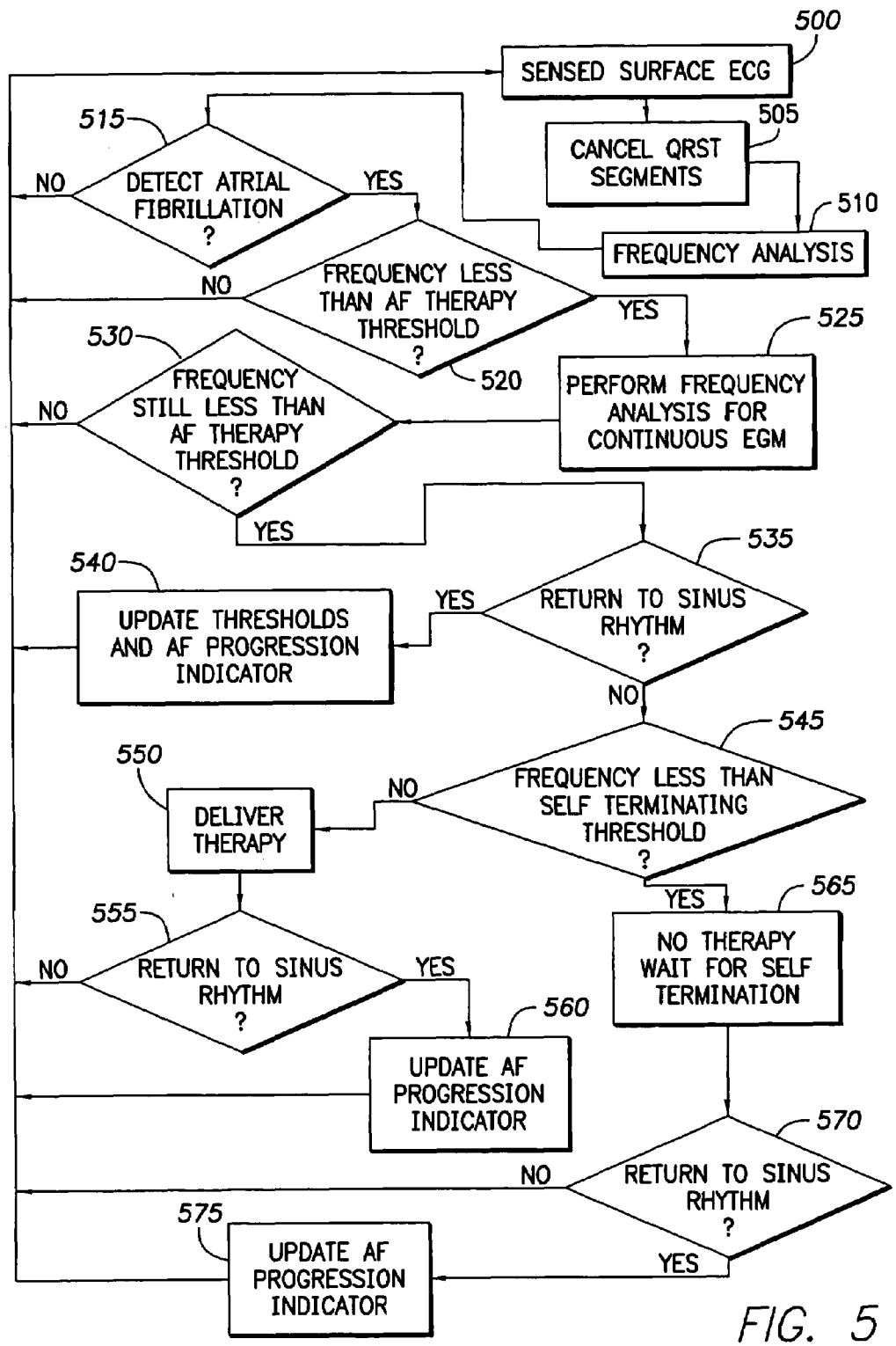
FIG. 5 is a flowchart showing a method for detecting atrial fibrillation events that are susceptible for termination based on the peak frequency of ECG segment in accordance with one embodiment of the present invention.

The present invention may also be practiced with an external monitor using ECG signals as illustrated in the flow chart of FIG. 5. In this embodiment the fibrillatory frequency is compared to thresholds set by the physicians that can be automatically optimized by the device based on mode switch episodes, the eventual outcome of fibrillation episodes or other events, to monitor how the atrial fibrillation event is progressing. If the frequency reaches a threshold deemed compatible with a propensity for termination but above another set of thresholds that indicate a propensity for self termination, a therapy such as anti-tachycardia pacing or cardioversion is delivered. Further this information is stored and used to track progression of disease.

Frequency domain analysis has previously been used with surface ECG data to characterize atrial fibrillation. However, surface ECG signals include both atrial and ventricular electrical activity. Therefore, one embodiment of the present invention cancels the QRST segment 505 of sensed ECG signals 500 to isolate the atrial electrical activity which can then be used to characterize atrial fibrillation signals.

In this embodiment Fourier analysis is used to calculate the peak frequency in the 3-9 Hz band of each ECG analysis window 510. In one embodiment, the micro-controller of the implantable device further analyzes the sensed ECG to detect the onset of atrial fibrillation 515.

If the patient is not in atrial fibrillation the device reverts to monitoring the sensed surface ECG 500. If the patient is in atrial fibrillation the micro-controller compares the peak frequency to an atrial fibrillation therapy threshold frequency 520, which discriminates between arrhythmias which are susceptible to termination and those which are not. In this embodiment if the peak frequency is greater than the atrial fibrillation therapy threshold the fibrillation episode is not likely to terminate, either naturally or through the application of a stimulation therapy. In this instance the device reverts to monitoring surface ECG signals 500.

If the peak frequency is less that the atrial fibrillation therapy threshold the micro-controller of the implantable device continuously analyzes the peak frequency for a predetermined period of time 525 to determine if the frequency remains less than the atrial fibrillation therapy threshold 530. In this embodiment if the peak frequency is greater than the atrial fibrillation therapy threshold during the predetermined period the implantable device reverts to monitoring surface ECG signals 500.

If the peak frequency is less than the atrial fibrillation therapy threshold throughout the pre-determined period, the micro-controller analyzes the ECG to determine whether the patient has returned to sinus rhythm 535. If the patient has returned to sinus rhythm the micro-controller updates the therapy threshold and a self termination threshold to reflect the rate at which the arrhythmia terminated. The device also updates an atrial fibrillation progression indicator histogram 540 to include statistics such as the length of the fibrillation episode, the maximum rate (and statistical variations thereof) as well as the atrial rate when the episode self-terminated. The device then returns to monitoring signals on the surface ECG 500.

However, if the patient does not return to sinus rhythm the micro-controller compares the peak frequency to a self terminating threshold 545. If the peak frequency is greater than a self terminating threshold the implantable device delivers anti-fibrillation therapy to terminate the arrhythmia 550. The micro-controller then determines if the patient has returned to sinus rhythm 555. If so the micro-controller updates an atrial fibrillation progression indicator histogram 560 to include statistics such as the length of the fibrillation episode, the maximum peak frequency during the episode (and statistical variations thereof as well as the stimulation therapy that successfully terminated the episode.

In this embodiment, if the peak frequency is below the self-terminating threshold the micro-controller withholds therapy and waits a predetermined period for the fibrillation episode to self-terminate 565 and for the patient to return to sinus rhythm 570. If so the micro-controller again updates the atrial fibrillation progression indicator histogram 575 to include statistics such as the length of the fibrillation episode, the maximum rate (and statistical variations thereof as well as the atrial rate when the episode self-terminated. If the patient does not return to sinus rhythm the micro-controller returns to monitoring the surface ECG signals 500.

While the invention herein disclosed has been described by means of specific embodiments and applications thereof, numerous modifications and variations could be made thereto by those skilled in the art without departing from the scope of the invention set forth in the claims. For example, the methods or algorithms described in connection with the embodiments disclosed herein may be embodied directly in hardware, in a software module executed by a processor, or in a combination of the two.

A software module may reside in RAM memory, flash memory, ROM memory, EPROM memory, EEPROM memory, registers, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for processing a patient's cardiac signals, comprising:
   detecting an ongoing episode of atrial fibrillation;
   determining a characteristic of the cardiac signals sensed during the ongoing episode of atrial fibrillation;
   comparing the characteristic to an atrial fibrillation therapy threshold;
   comparing the characteristic to a self-termination threshold if the characteristic is less than or equal to the atrial fibrillation therapy threshold; and
   withholding anti-tachycardia therapy if the characteristic of the cardiac signals sensed during the ongoing episode of atrial fibrillation is less than the self-termination threshold.

2. The method of claim 1 further comprising delivering anti-tachycardia therapy if the characteristic is greater than or equal to the self-termination threshold.

3. The method of claim 1 wherein determining a characteristic of the cardiac signals comprises determining cardiac heart rate.

4. The method of claim 1 wherein determining a characteristic of the cardiac signals comprises determining peak frequency of the cardiac signals.

5. The method of claim 4 further comprising canceling a QRST segment of the cardiac signals.

6. The method of claim 1 further comprising determining whether the patient returned to sinus rhythm in response to delivery of the anti-tachycardia therapy.

7. The method 6 further comprising updating an atrial fibrillation progression histogram to monitor progression of the atrial fibrillation.

8. The method of claim 2 further comprising determining whether the patient returned to sinus rhythm in response to with-holding delivery of the anti-tachycardia therapy.

9. The method 8 further comprising updating an atrial fibrillation progression histogram to monitor progression of the atrial fibrillation.

10. The method of claim 9 wherein updating an atrial fibrillation progression histogram comprises storing termination mechanism and characteristic of cardiac signal at termination.

11. The method of claim 6 further comprising activating an implantable drug pump to administer an anti-tachycardia drug if the patient does not return to sinus rhythm.

12. The method of claim 1 further comprising generating the atrial fibrillation therapy threshold and the self-termination threshold from a database of cardiac signals.

13. The method of claim 7 further comprising adjusting at least one of the atrial fibrillation therapy threshold and the self-termination threshold in response to data stored in the atrial fibrillation progression histogram.

14. The method of claim 9 further comprising adjusting at least one of the atrial fibrillation therapy threshold and the self-termination threshold as a function of data stored in the atrial fibrillation progression histogram.

15. The method of claim 1 further comprising monitoring the characteristic of the cardiac signals to determine if the characteristic is less than or equal to the atrial fibrillation therapy threshold for a predetermined period, wherein comparing the characteristic to the self-termination threshold comprises comparing the characteristic to the self termination threshold if the characteristic is less than or equal to atrial fibrillation therapy threshold for a predetermined period.

16. A medical device for monitoring a patient's cardiac signals, comprising:
    means for detecting an ongoing episode of atrial fibrillation;
    means for determining a characteristic of the cardiac signals sensed during the ongoing atrial fibrillation episode;
    means for comparing the characteristic to an atrial fibrillation therapy threshold;
    means for comparing the characteristic to a self-termination threshold if the characteristic is less than or equal to the atrial fibrillation therapy threshold; and
    means for with-holding anti-tachycardia therapy if the characteristic of the cardiac signals sensed during the ongoing episode of atrial fibrillation is less than the self-termination threshold.

17. The device of claim 16 further comprising means for monitoring the characteristic of the cardiac signals to determine if the characteristic is less than or equal to the atrial fibrillation therapy threshold for a predetermined period, wherein the means for comparing the characteristic to the self-termination threshold comprises means for comparing the characteristic to the self termination threshold if the characteristic is less than or equal to atrial fibrillation therapy threshold for a predetermined period.

18. The device of claim 16 further comprising means for delivering anti-tachycardia therapy if the characteristic is greater than or equal to the self-termination threshold.

19. The device of claim 16 wherein the means for determining a characteristic of the cardiac signals comprises means for determining cardiac heart rate.

20. The device of claim 16 wherein the means for determining a characteristic of the cardiac signals comprises means for determining peak frequency of the cardiac signals.

21. A medical device for monitoring a patient's cardiac signals, comprising:
    a rhythm detector for detecting an ongoing episode of atrial fibrillation;
    sensor for determining a characteristic of the cardiac signals sensed during the ongoing episode of atrial fibrillation; and
    a controller coupled to the sensor, the controller being adapted to compare the characteristic to a atrial fibrillation therapy threshold and if the characteristic is less than or equal to the atrial fibrillation therapy threshold for further comparing the characteristic to a self termination threshold and wherein the controller with-holds delivery of anti-tachycardia therapy if the characteristic of the cardiac signals sensed during the ongoing episode of atrial fibrillation is less than the self-termination threshold.

22. The device of claim 21 further comprising an atrial pulse generator for delivering anti-tachycardia therapy if the characteristic is greater than or equal to the self-termination threshold.

23. A method for processing a patient's cardiac signals, comprising:
    detecting an ongoing episode of atrial fibrillation;
    determining a characteristic of the cardiac signals sensed during the ongoing episode of atrial fibrillation;
    comparing the characteristic to an atrial fibrillation therapy threshold; and
    withholding therapy if the characteristic of the cardiac signals sensed during the ongoing episode of atrial fibrillation is greater than the atrial fibrillation therapy threshold.

24. The method of claim 23 further comprising comparing the characteristic to a self-termination threshold if the characteristic is less than or equal to the atrial fibrillation therapy threshold and withholding anti-tachycardia therapy if the characteristic is less than the self-termination threshold.

25. The method of claim 24 further comprising delivering anti-tachycardia therapy if the characteristic is greater than or equal to the self-termination threshold and less than or equal to the atrial fibrillation therapy threshold.

\* \* \* \* \*